United States Patent
Baker et al.

(10) Patent No.: US 7,322,527 B2
(45) Date of Patent: Jan. 29, 2008

(54) COLOR MEASUREMENT INSTRUMENT CAPABLE OF BOTH STRIP READING AND SPOT READING

(75) Inventors: Douglas V. Baker, Middleville, MI (US); Michael J. Weber, Rockford, MI (US); Todd A. Sutton, Grand Rapids, MI (US); Paul D. Newton, Grand Rapids, MI (US)

(73) Assignee: X-Rite, Inc., Grand Rapids, MI (US)

( * ) Notice: Subject to any disclaimer, the term of this patent is extended or adjusted under 35 U.S.C. 154(b) by 204 days.

(21) Appl. No.: 11/116,866

(22) Filed: Apr. 28, 2005

(65) Prior Publication Data

US 2005/0242191 A1    Nov. 3, 2005

Related U.S. Application Data

(60) Provisional application No. 60/567,416, filed on Apr. 30, 2004.

(51) Int. Cl.
*G06K 7/10*    (2006.01)
(52) U.S. Cl. ............. 235/472.01; 235/454; 235/462.43; 235/462.44; 235/462.45
(58) Field of Classification Search ............... 235/454, 235/462.43–462.45, 472.01
See application file for complete search history.

(56) References Cited

U.S. PATENT DOCUMENTS

| | | | |
|---|---|---|---|
| 4,538,072 A * | 8/1985 | Immler et al. .............. 250/568 |
| 5,646,735 A | 7/1997 | Krzyminski | |
| 5,814,804 A * | 9/1998 | Kostizak ................ 235/472.01 |
| 5,844,681 A | 12/1998 | Alessi et al. | |
| 5,955,719 A * | 9/1999 | Southworth et al. ........ 235/454 |
| 6,061,140 A * | 5/2000 | Berg et al. ................... 356/418 |
| 6,285,452 B1 * | 9/2001 | Baker .......................... 356/402 |
| 6,362,886 B2 * | 3/2002 | Ruevski et al. ............. 356/402 |
| 7,070,110 B2 * | 7/2006 | Lapstun et al. ......... 235/462.45 |
| 2001/0015806 A1 | 8/2001 | Baker | |
| 2002/0005950 A1 * | 1/2002 | Beimers et al. ............. 356/402 |
| 2002/0036778 A1 * | 3/2002 | Wagner et al. ............. 356/406 |
| 2003/0071998 A1 * | 4/2003 | Krupka et al. .............. 356/402 |

OTHER PUBLICATIONS

Spectrolino Spectrophotometer, The Handheld System That Scores High In Color Measurement Precision (GretagMacbeth).

* cited by examiner

*Primary Examiner*—Michael G. Lee
*Assistant Examiner*—Tuyen K Vo
(74) *Attorney, Agent, or Firm*—McCarter & English, LLP

(57) ABSTRACT

A color measurement instrument that is capable of both spot reading and strip reading. The instrument includes a handheld unit and a docking unit. When removed from the docking unit, the handheld unit is used for spot reading. When docked in the docking unit, the handheld unit and the docking unit are used together for strip reading. The handheld unit includes a self-storing target that is deployed for spot reading and stored for strip reading. The handheld unit also includes a self-storing calibration plaque that is deployed for calibration and stored otherwise. When docked, the handheld unit teeters on the docking unit between a normally closed position and a manually selectable open position to accommodate a variety of sample thicknesses.

6 Claims, 10 Drawing Sheets

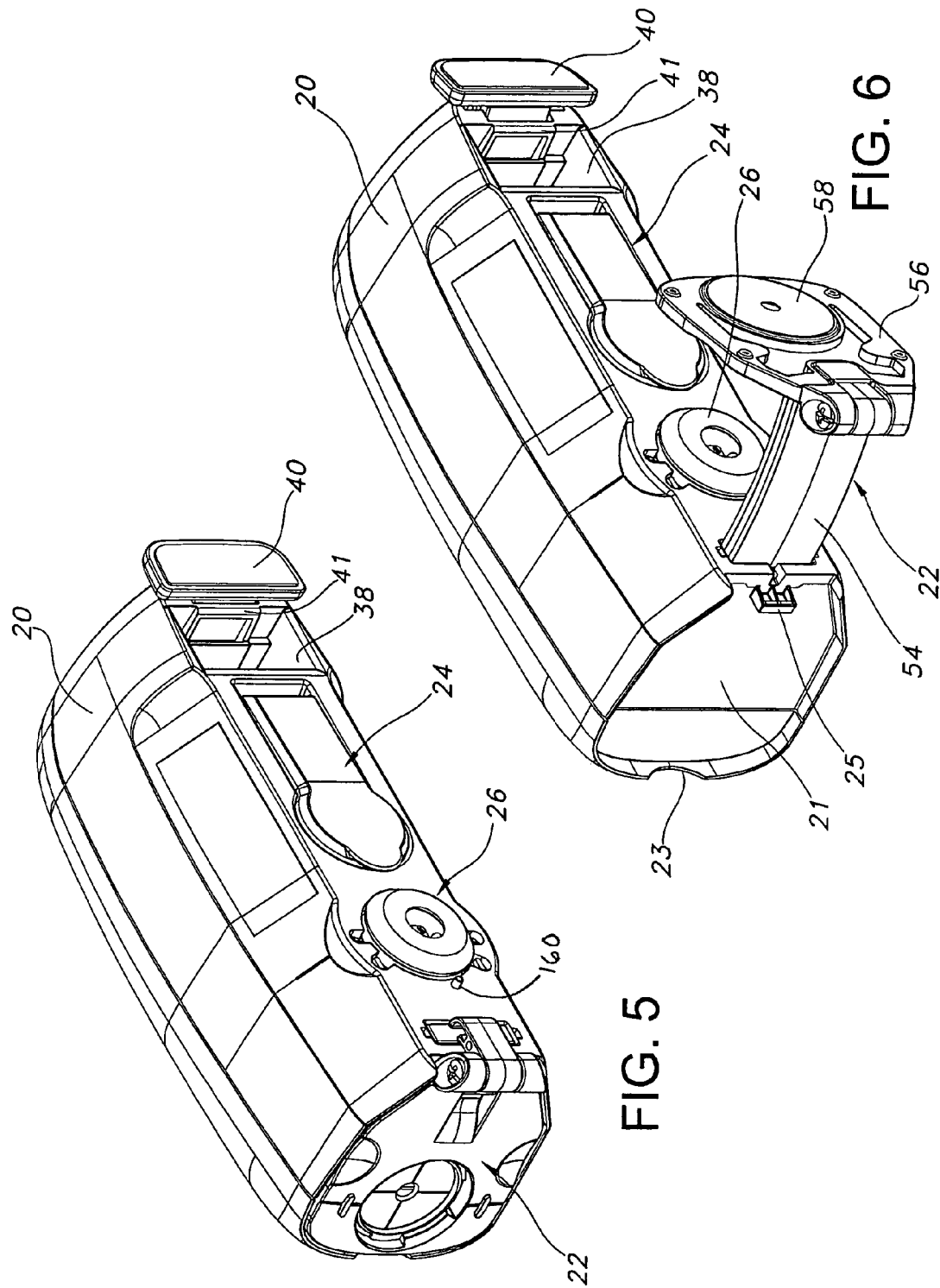

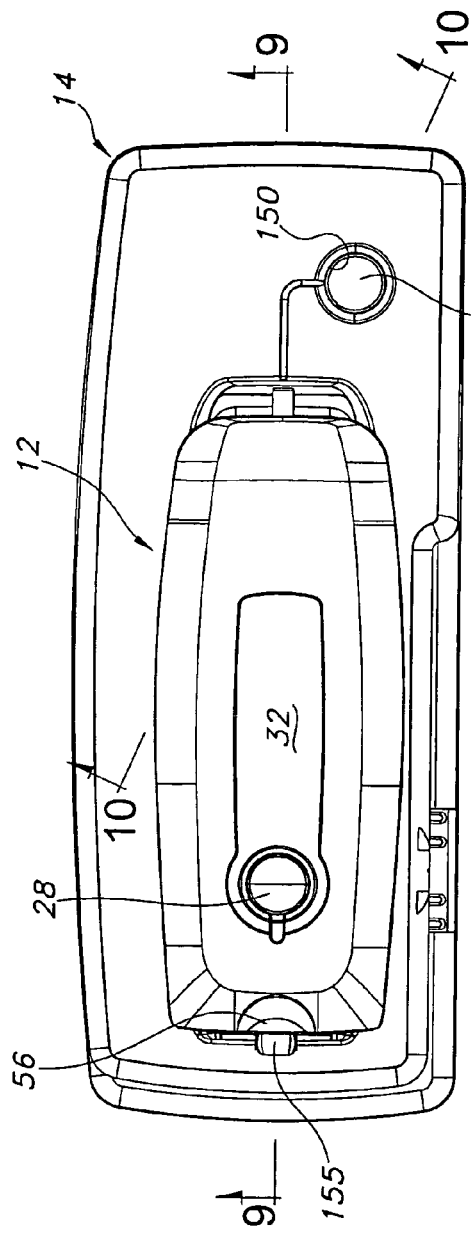
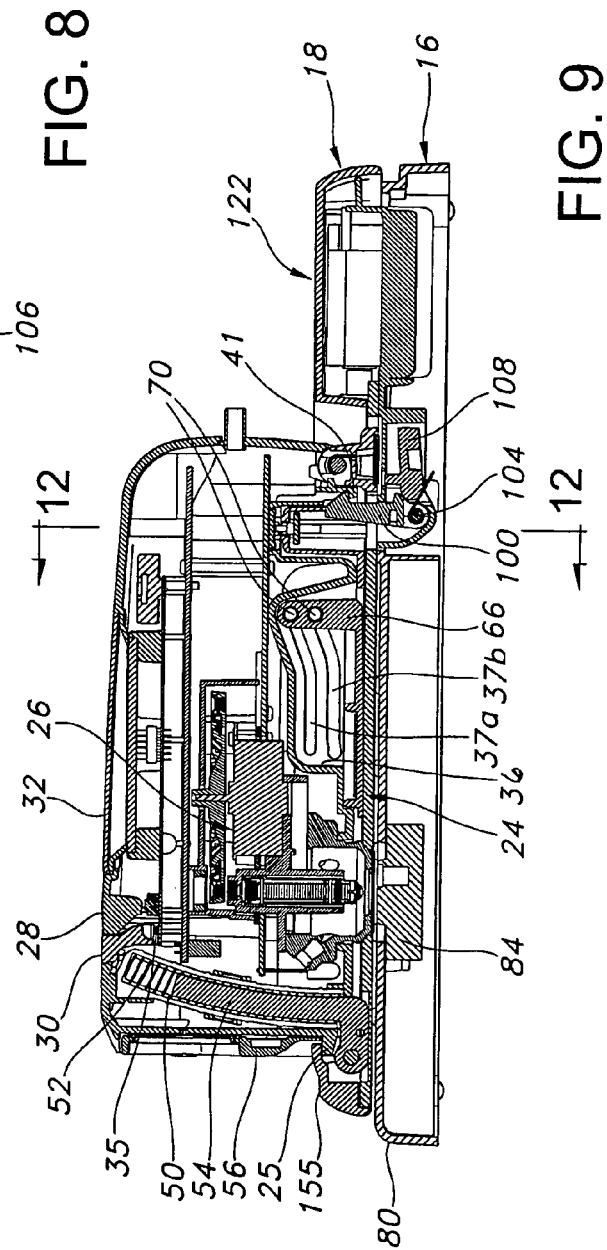
FIG. 8
FIG. 9

COLOR MEASUREMENT INSTRUMENT CAPABLE OF BOTH STRIP READING AND SPOT READING

This application claims the benefit of provisional application No. 60/567,416 filed Apr. 30, 2004, and entitled "Color Measurement Engine Capable of Both Strip Reading and Spot Reading."

BACKGROUND OF THE INVENTION

The present invention relates to color measurement instruments, and more particularly to strip reading color measurement instruments and spot reading color measurement instruments.

A wide variety of color measurement instruments are known for many and varied applications. These instruments are used, for example, to accurately determine the color of materials such as printed matter, photographic matter, paints, textiles, and plastics. More specifically, the instruments measure the spectral distribution within the visible color spectrum of light reflected by, or transmitted through, a sample. The color measurement engines within color measurement instruments can be spectrophotometers, colorimeters, densitometers, or other devices used to measure color.

One type of color measurement instrument is a strip reading instrument. Such an instrument typically sits on a horizontal surface (e.g. a countertop) and draws a strip to be measured through the instrument and past a color measurement engine. The engine periodically measures the color of the moving strip. An exemplary strip reading instrument is disclosed in U.S. Pat. No. 6,198,536 issued Mar. 6, 2001 to Baker.

A second type of color measurement instrument is a spot reading instrument. Such an instrument is typically a handheld unit that can be aligned with a particular color or spot to be measured. When manually aligned, the instrument is actuated to read the color or spot.

Both strip reading instruments and spot reading instruments are dedicated to a single function (e.g. strip reading or spot reading). Consequently, a user desiring to read both strips and spots must purchase two separate instruments.

Spot reading instruments typically include a spring-loaded shoe that carries a targeting system to assist the user in accurately positioning the instrument with respect to the spot to be measured. After being accurately positioned, the instrument is closed against the shoe, overcoming the spring force. The measurement is taken when the instrument is closed against the shoe. The shoe provides precise vertical positioning of the optics in the instrument with respect to the read plane of the sample being measured. The instrument is then released whereupon the spring-loaded shoe reopens the instrument. The shoe and targeting system typically are intended to remain connected to the instrument. However, on certain occasions, removal of the shoe and target may be desired. When the shoe is removed, it is subject to damage, soiling, and possible loss.

All color measurement instruments must be calibrated from time to time. Such calibration usually is performed using one or more reference colors, whose properties are known. During calibration, the instrument reads the reference color(s) and then configures itself based on the differences between the known properties and the measured properties. Typically, the references colors are used relatively infrequently, which results in several problems. First, the reference colors can be misplaced. Second, the reference colors can be damaged, for example, by scratching. Third, the references colors can become soiled. Both damage and soiling can damage the reference color(s), thereby decreasing the accuracy and thereby the utility of the calibration function.

SUMMARY OF THE INVENTION

The aforementioned problems are overcome in the present invention in which a color measurement instrument is capable of both strip reading and spot reading.

In a first aspect of the invention, the instrument includes a handheld unit and a docking unit. The handheld unit, when out of the docking unit, can be used for spot reading. The handheld unit can be docked in the docking unit so that the instrument can be used for strip reading.

In a second aspect of the invention, the handheld unit includes a self-storing target system that is movable between a stored position and an operative position. In the stored position, the target system does not interfere with docking the unit in the docking unit. When the unit is undocked for spot reading, the target system can be moved to the operative position.

In a third aspect of the invention, the handheld unit also includes a self-storing reference color or calibration plaque. The plaque can be moved between a storage position and a calibration position. In the storage position, the calibration plaque is protected from damage or soiling, while still being readily accessible for calibration at any time. In the calibration position, the plaque is positioned over the color measurement engine.

In a fourth aspect of the invention, the docking unit includes a base and a cradle that "teeter-totters" on the base to define a strip opening therebetween. Normally under the mass of the handheld unit, the cradle is in the operative position with respect to the base for strip reading. However, the cradle can be "teetered" to an open position above the base by pressing on one end of the cradle. This construction facilitates the insertion of unusually thick or thin sample media into the instrument, and also permits opening of the strip transportation area to correct misfeeds and jams, to realign strips, or simply to visually inspect the instrument.

These and other objects, advantages, and features of the invention will be more fully understood and appreciated by reference to the description of the current embodiment and the drawings.

BRIEF DESCRIPTION OF THE DRAWINGS

FIG. 5 is a perspective view of the underside of the handheld unit showing the flip-down target and calibration plaque in their stored positions;

FIG. 6 is a view similar to FIG. 5 but showing the flip-down target in the operative position;

FIG. 8 is a top plan view of the instrument;

FIG. 9 is a sectional view taken along line IX-IX in FIG. 8;

DESCRIPTION OF THE CURRENT EMBODIMENT

Figure 1:
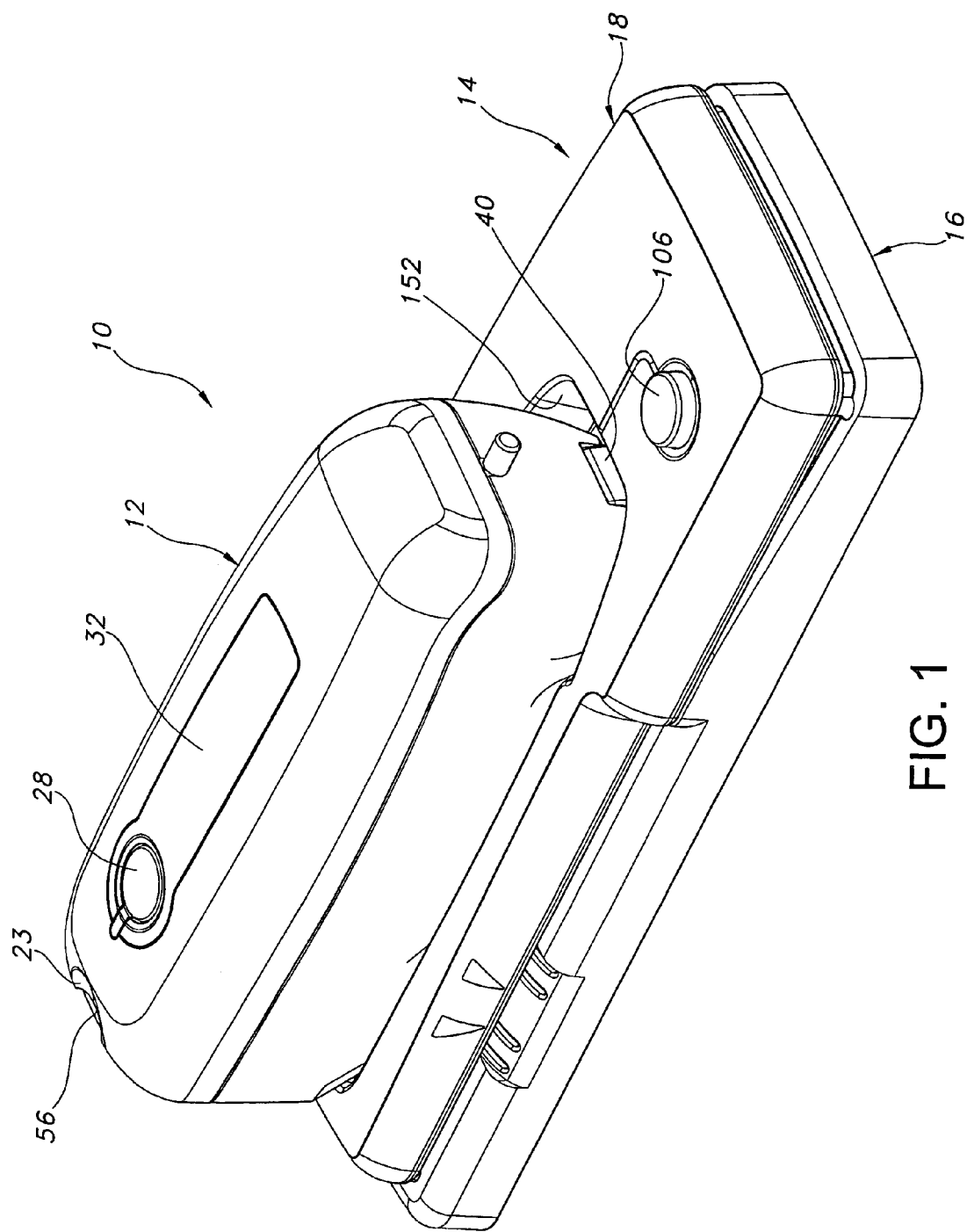
FIG. 1 is a perspective view of the color measurement instrument of the present invention.
Figure 2:
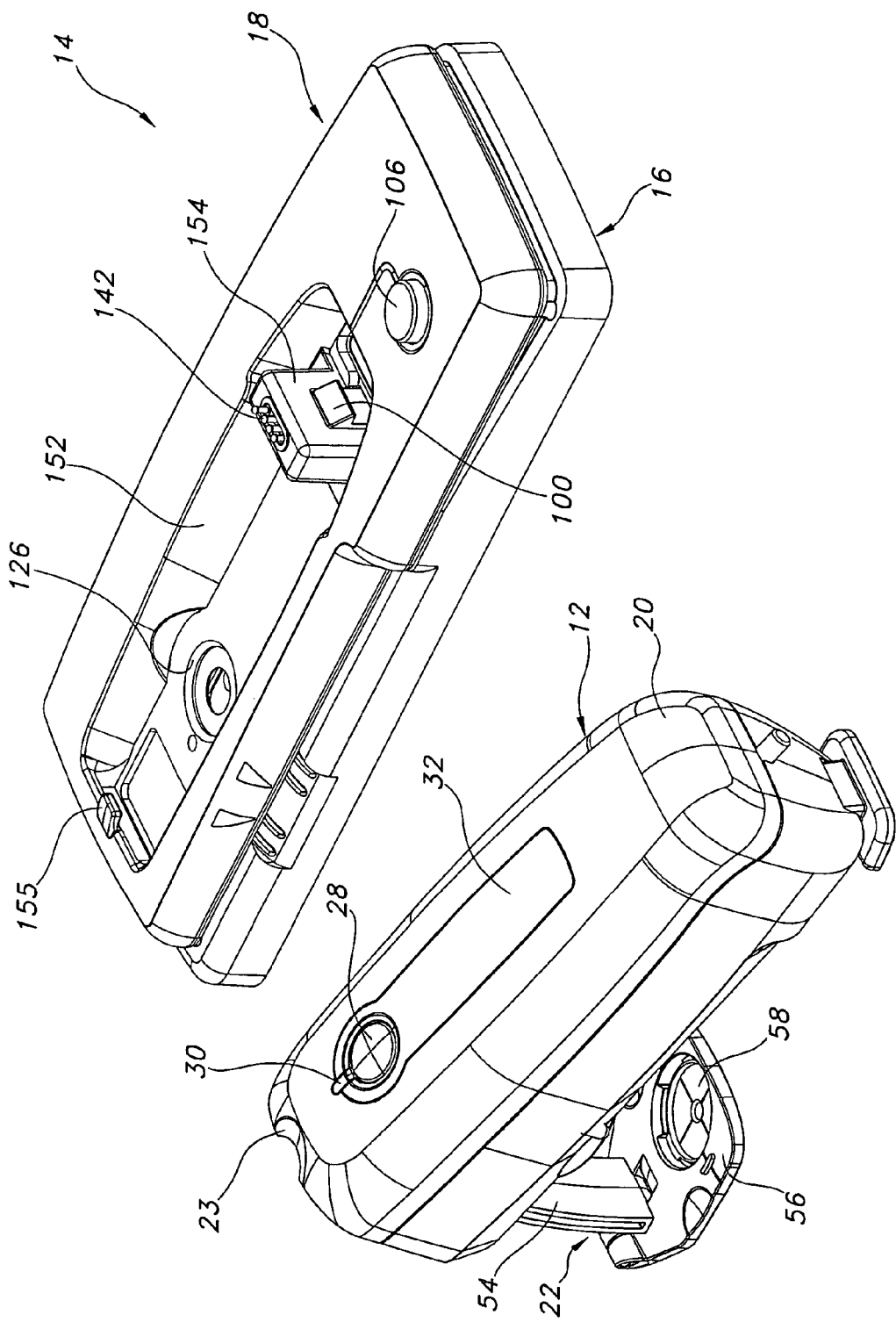
FIG. 2 is a perspective view of the handheld unit removed from the docking unit.

A color measurement instrument constructed in accordance with a current embodiment of the invention is illustrated in the drawings and generally designated 10. The instrument includes a handheld unit 12 and a docking unit 14. The docking unit in turn includes a base 16 and a cradle 18 supported on the base. The handheld unit 12 can be docked in the docking unit 14 (FIG. 1). When so docked, the instrument 10 is capable of operating as a strip reading instrument. The handheld unit 12 can be removed from the docking unit 14 (FIG. 2). When undocked, the handheld unit 12 is capable of operating as a spot reading instrument.

The handheld unit 12 includes a housing 20, a flip-down target system 22, and a self-storing calibration plaque assembly 24. The flip-down target system is movable between a stored position illustrated in FIGS. 5 and 7 when the unit is to be used as a strip reader, and an operative position illustrated in FIGS. 2 and 6 when the unit is to be used as a spot reader.

Figure 7:
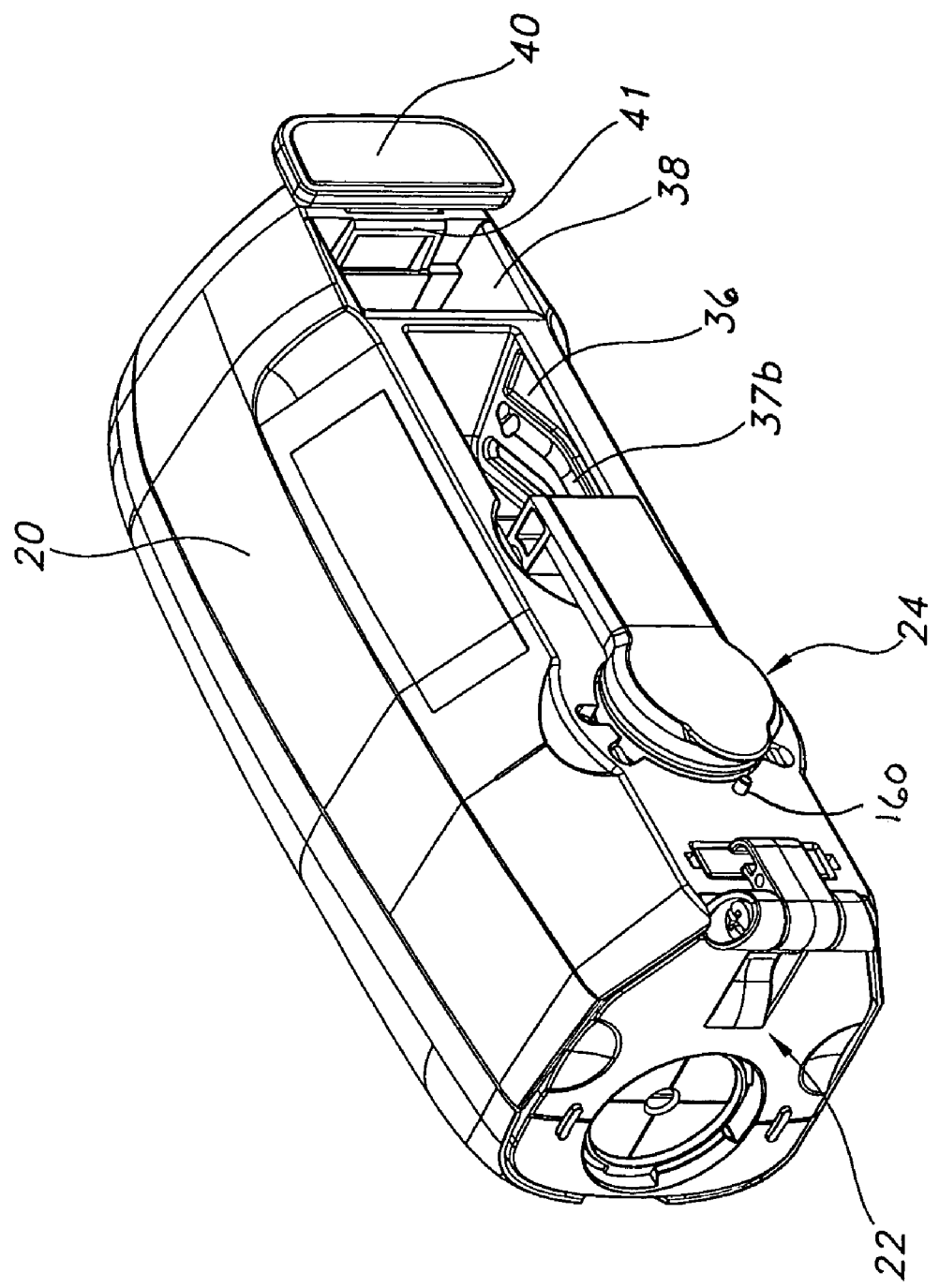
FIG. 7 is a view similar to FIG. 5 but showing the calibration plaque in the calibration position.
Figure 11:
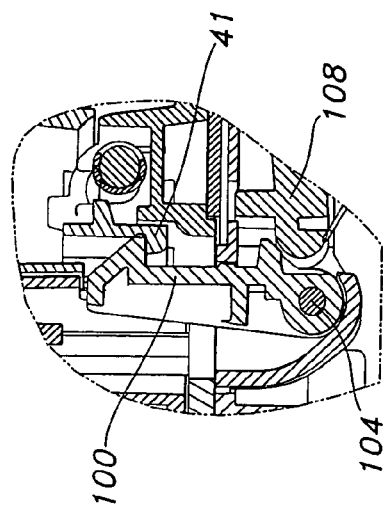
FIG. 11 is an enlarged sectional view of the area within line XI in FIG. 10.
Figure 13:
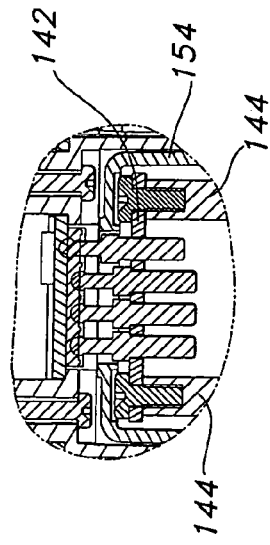
FIG. 13 is an enlarged sectional view of the area within line XIII in FIG. 12.
Figure 10:
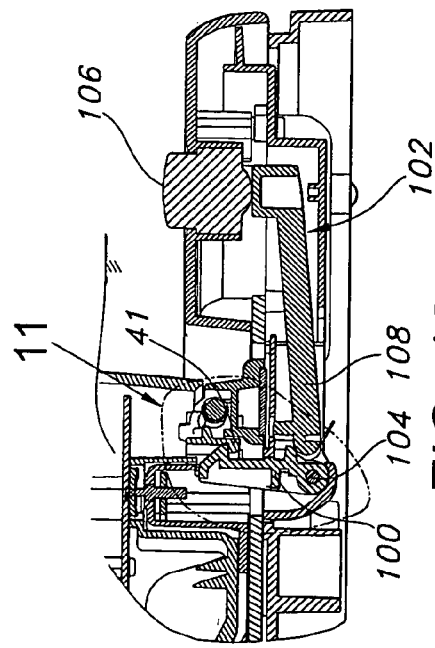
FIG. 10 is a fragmentary sectional view taken along line X-X in FIG. 8.
Figure 12:
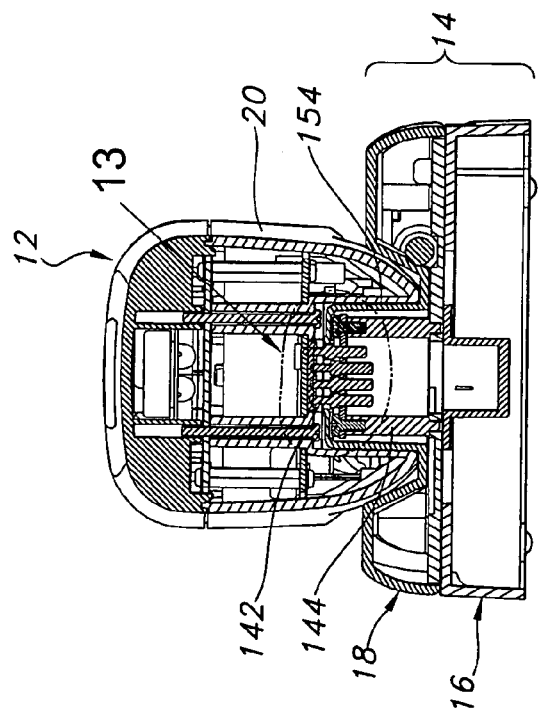
FIG. 12 is a sectional view taken along line XII-XII in FIG. 9.

The calibration plaque assembly is also movable between a stored position illustrated in FIGS. 5-6, and a calibration position illustrated in FIG. 7 in which the calibration plaque is aligned with the color measurement engine for instrument calibration.

I. Handheld Unit

Figure 3:
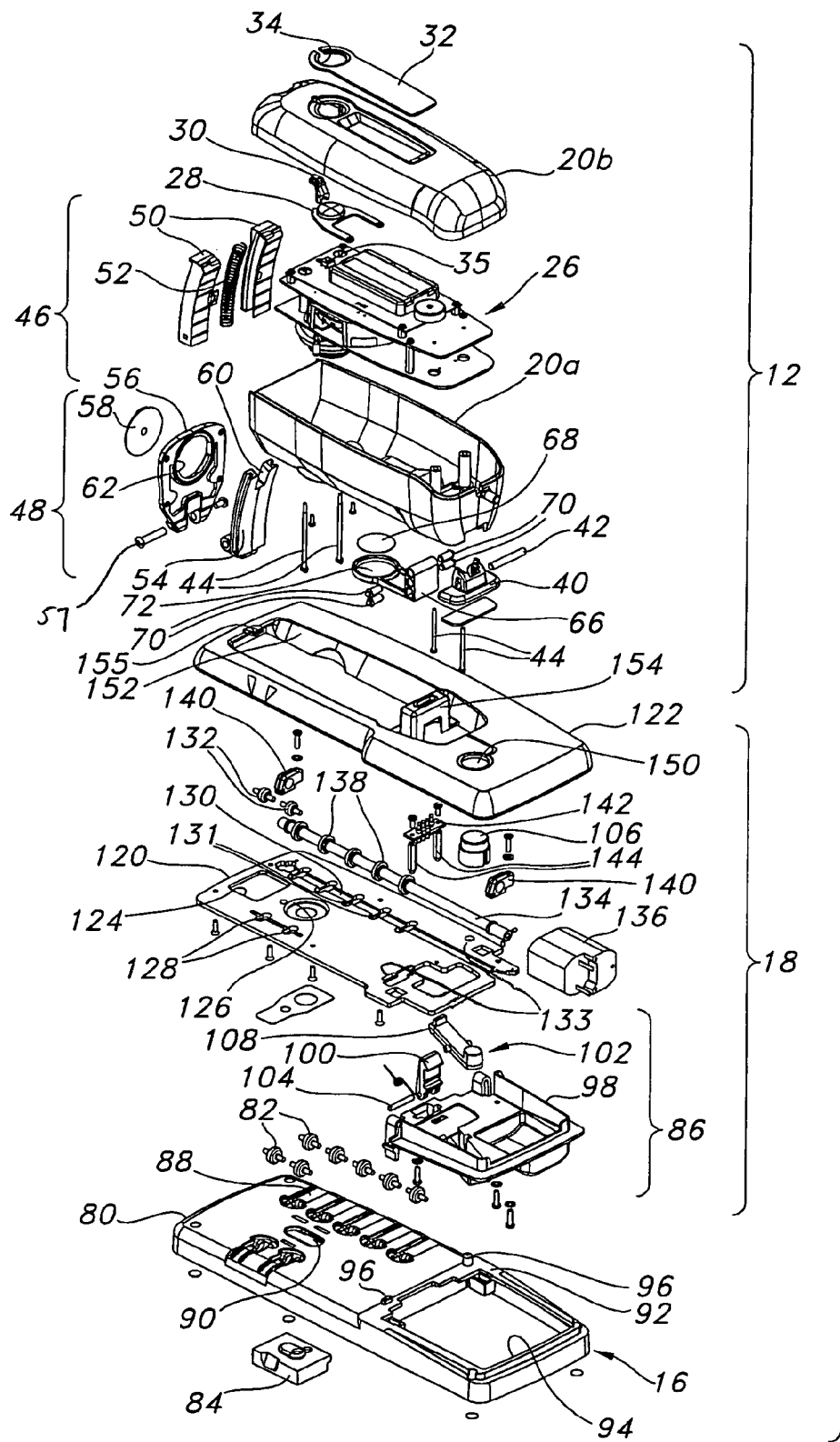
FIG. 3 is an upper perspective exploded view of the instrument.
Figure 4:
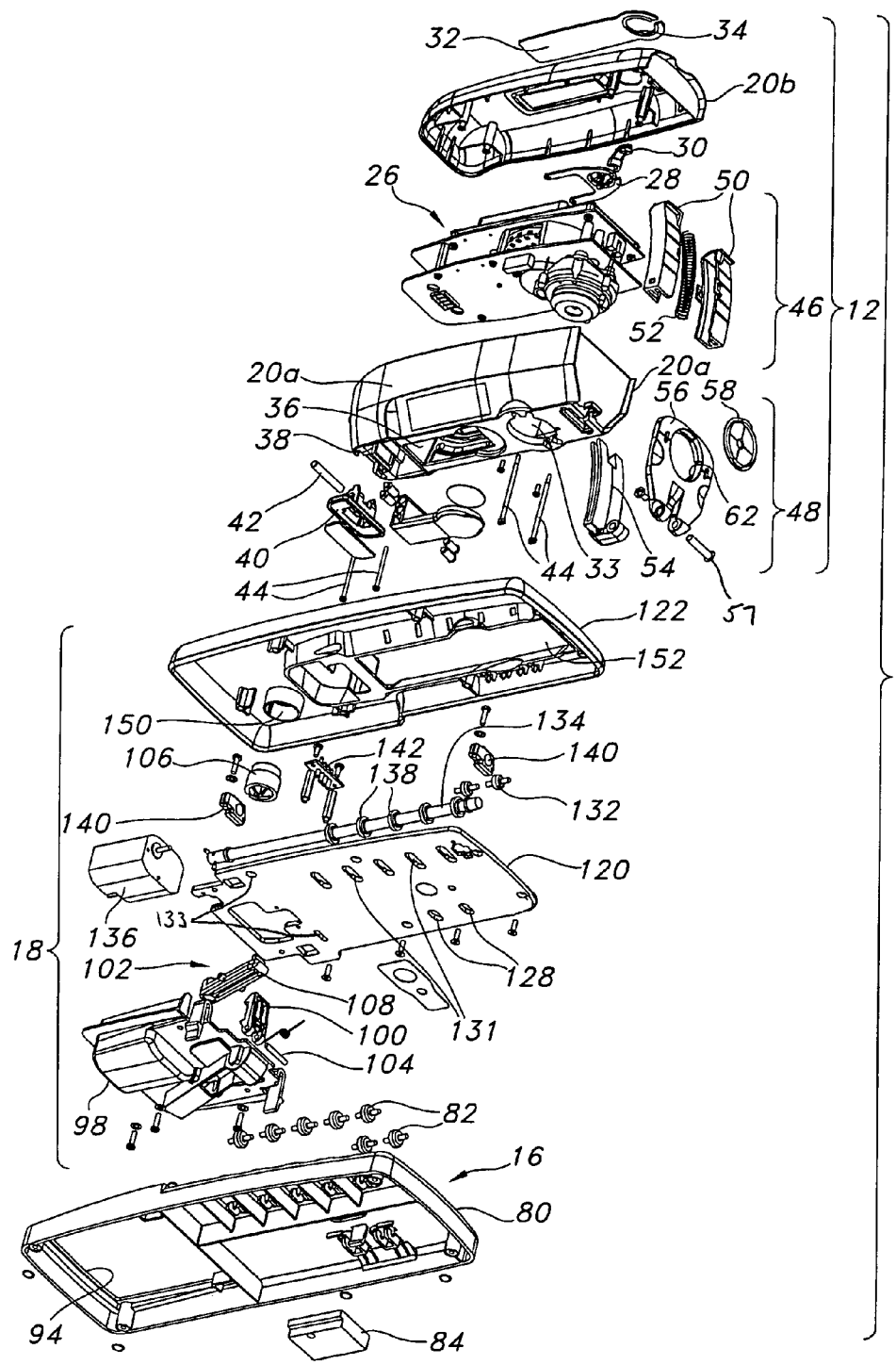
FIG. 4 is a lower perspective exploded view of the instrument.

The components within the handheld unit 12 are illustrated in detail in FIGS. 3-4. The housing 20 includes a lower housing half 20a and an upper housing half 20b. The housing halves interfit with one another to define the housing, which encapsulates and/or supports the other components of the handheld unit 12. The forward face of the housing 20 defines a storage recess 21 (see FIG. 6) in which the target system 22 is fitted when the target system is in the storage position (see FIGS. 5 and 7). The housing 20 also defines a finger access 23 communicating with the recess 21 to provide a point at which the target system 22 can be accessed when in the storage position. The housing 20 further includes a projection 25 in the lower portion of the recess 21 to cooperate with the target system 22 when in the storage position to assist in retaining the target system in the recess.

A color measurement engine 26 is contained and supported within the housing 20. The color measurement engine can be of any type generally known in the art including a spectrophotometer, a colorimeter, or a densitometer. In the current embodiment, the color measurement instrument 26 is a spectrophotometer of a type generally included in a variety of instruments manufactured and sold by X-Rite, Incorporated, the assignee of the present application. Other suitable engines are well known to those skilled in the art.

A plurality of screws 44 extend through the lower body half 20a and into the upper body half 20b to intersecure the two halves and the color measurement engine 26 located therein.

The handheld unit 12 further includes a push button 28, a light pipe 30, and a clear window trim plate 32. The trim plate 32 is mounted in the upper portion of the upper body half 20b and defines an aperture 34 through which the button 28 may be accessed. The light pipe 30 displays the current color of the status LED(s) 35 on the engine 26. The push button is depressed when a strip reading measurement is to be taken.

The lower body half 20a includes an engine aperture 33, a calibration arm pocket 36, and a connection pocket 38. The color measurement instrument 26 is positioned within the aperture 33. The calibration arm pocket 36 defines upper and lower pairs of opposite grooved tracks 37a and 37b (see FIGS. 7 and 9) that guide the movement of the calibration assembly, which is mounted within the pocket 36. The connection pocket 38 is aligned with a connection mount on the docking station 14, and electrical connectors within the pocket 38 and on the mount interfit with one another when the handheld unit is docked in the docking station 14. Within the connection pocket 38 is a catch 41, which is engaged and secured by the latch 100 when the handheld unit is docked in the docking station 14.

A foot 40 is hingedly mounted to the lower body half 20a at the lower rear corner of the housing 20 on a hinge pin 42. The foot 40 provides a support for the handheld unit 10 during spot reading.

The flip-down target system 22 includes a receiver assembly 46 and a target assembly 48 (see FIGS. 3-4). The receiver assembly 46 includes a pair of tracks 50 fixedly secured within the body 20, and a coil spring 52 urging the target assembly 48 to its operative position as illustrated in FIGS. 2 and 6. The target assembly includes a telescoping arm 54, a foot 56, and a reticule 58. The telescoping arm 54 is fitted between and rides within the tracks 50. The upper portion of the arm 54 defines a slot 60 for receiving the lower end of the spring 52. The foot 56 defines an aperture 62 in which the reticule 58 is mounted in conventional fashion. The foot 56 is hingedly mounted on the lower end of the arm 54 on a screw 57. The friction fit between the arm 54 and the foot 56 retains the foot 56 in the operative position unless the foot is positively moved out of the operative position.

The target system can be moved between the stored position illustrated in FIGS. 5 and 7 and the operative position illustrated in FIGS. 2 and 6. When in the stored position, the arm 54 is telescopically received within the housing 20 and between the tracks 50; and the foot 56 is rotated to fit within the foot recess 21 in the housing 20. The inter-engagement of the foot 56 and the projection 25 (see FIG. 6) retains the target system 22 in the storage position. The target system 22 can be deployed to the operative position by removing the foot 56 from the pocket 21. The foot 56 can be pushed from the pocket 22 at the finger access 23 and manually rotated approximately 270 degrees with respect to the arm 54 until the foot is in the operative position; and the spring 52 (FIGS. 3-4) pushes the arm 54 to its fully extended position.

The calibration arm assembly 24 includes an arm 66, a calibration plaque or reference color 68, and four spring-loaded detent buttons 70. The arm 66 is generally L-shaped when viewed from the side. The vertical leg of the L supports the four detent buttons 70 with two—one above the other—on each side. The horizontal leg of the L defines an upwardly opening pocket 72 in which the calibration plaque 68 is secured. The two upper detent buttons ride in the tracks 37a, and the two lower detent buttons ride in the tracks 37b, to define the travel path of the arm as the calibration assembly 24 moves between its storage position (FIGS. 5-6) and its calibration position (FIG. 7). The calibration assembly can be moved to a cleaning position (not shown) between the storage position and the calibration position in which the assembly extends generally perpendicularly from the body 20. The lower detents 70 must be moved outside of the lower track 37b to move the calibration assembly to the cleaning position. The calibration plaque 68 is easily viewable and accessible in the cleaning position. Additionally, the assembly 24 may be separated from the housing 20 altogether for service or replacement.

II. Docking Unit

The docking unit includes a base 16 and a cradle 18 supported in teeter-totter fashion on the base.

The base 16 includes a base body 80, a plurality of idler rollers 82, and a backer 84. The base body 80 defines a lock-receiving aperture 94 and includes a plurality of integrally molded flexible arms 88. Each arm supports one of the idler rollers 82. The backer 84 is mounted on the underside of the base body 80 and is aligned with the race-track shaped aperture 90 to provide a selectable backer color and/or material for the color measurement engine 26. The base body 80 also includes a fulcrum or teeter platform 92. A pair of locator pins 96 extend upwardly from the teeter platform 92 to interfit with the cradle 18.

The function and operation of the base 80, the idler rollers 82, and the backer 84 are generally analogous to the corresponding components disclosed and described in U.S. Pat. No. 6,198,536 issued Mar. 6, 2001 to Baker, the disclosure of which is incorporated by reference.

The cradle 18 includes a base plate 120, a drive assembly, a cover 122, and a lock assembly 86.

The base plate 120 defines a pocket 124, an engine pocket 126, roller openings 128, drive shaft pocket 130, and shaft drive wheel openings 131. The engine pocket 126 provides a physical reference to register with the optical portion of the color measurement instrument 26. A pair of idler rollers 132 are supported in the idler roller pockets 128 for engagement with the corresponding idler rollers 82 in the base body 80. The base plate 120 further defines locator apertures 133 that interfit with the pins 96 on the base 16 to properly locate the cradle 18 on the base. The base plate rests on the fulcrum or teeter platform 92 on the base 16.

The drive assembly includes a drive shaft 134 and a motor 136 for selectively driving the shaft. The drive shaft 134 includes a plurality of O-rings 138 which act as wheels or tires. The drive shaft 134 is mounted in the drive shaft pocket 130 so that the O-rings 138 are located within the drive shaft wheel openings 131 to extend from the underside of the base plate 120. A pair of journals 140 are secured to the base plate 120 over the drive shaft 134 to retain the drive shaft in position. When docked, the mass of the handheld unit 12 is additionally supported on the idler rollers 82 through the O-rings 138

An electrical connector 142 is mounted on a pair of studs 144 to provide electrical connection with the handheld unit 12 when the handheld unit is docked in the docking unit 14.

The cover 122 defines a button opening 150 and a cradle opening 152, and includes an electrical connector mount 154. A toe 155 extends into the cradle opening from the forward portion of the cradle opening to cooperate with the projection 25 on the handheld unit 12 to secure the handheld unit in the docking station.

The lock mechanism 86 includes a body 98, a latch 100, and an actuator arm 102. The body 98 is secured to the base plate 120. The latch 100 is hingedly connected to the body 98 on a hinge pin 104. The actuator arm 102 includes a button 106 located within the aperture 150, and a remote end 108 engaging the latch 100. The latch interfits with and releasably secures the catch 41 on the housing 20 when the handheld unit 12 is docked in the docking unit 14. When the button 106 is depressed, the arm 108 pushes the latch 100 to disengage the catch 41.

FIGS. 9-13 are sectional views of the handheld unit 12 docked or secured within the docking unit 14. When docked, the projection 25 on the handheld unit 12 is positioned under the toe 155 on the cover 122, and the catch 41 is secured by the latch 100.

OPERATION

The instrument 10 can be used as either a strip reading instrument or a spot reading instrument. To operate the instrument in the strip reading mode, the handheld unit 12 is docked in the docking unit 14. Specifically, the projection 25 on the forward portion of the handheld unit 12 is positioned under the toe 155 on the cradle cover 122. The heel of the instrument is then pressed downwardly until the latch 100 fits over and secures the catch 41.

When so docked, the instrument 10 can be operated as a strip reading instrument in a manner generally similar to that described in U.S. Pat. No. 6,198,536 by actuating the button 28. Specifically, the motor 136 is actuated to rotate the shaft 134. A strip is inserted between the base 16 and the cradle 18. The wheels 138 on the drive shaft 134 draw the sample through the instrument past the color measurement engine 26. The engine samples the strip at locations along the strip to make color measurements. The control and color measurement software required to operate the instrument 10 as a strip reader are well known to those skilled in the art.

To operate the instrument 10 as a spot reader, the handheld unit 12 is removed or undocked from the docking unit 14. More specifically, the button 106 is depressed so that the latch 100 releases the catch 41. This permits the heel of the handheld unit 12 to be raised and subsequently the projection 25 to be removed from under the toe 155.

When removed from the docking unit, the handheld unit 12 can be used as a spot reader. The flip-down target system 22 is deployed from the storage position to the operative position by removing the foot 56 from the recess 21 in the forward portion of the body 20. Under the influence of the spring 52, the target arm 54 extends from the body 20. The user manually rotates the foot 56 approximately 270 degrees to place the target system in the operative position as illustrated in FIGS. 2 and 6. At this point, the unit 12 is ready for spot reading. The reticule 58 in the foot 56 is aligned with a spot or target area to be measured. When properly aligned, manual or hand pressure is applied to the handheld unit 10 to overcome the spring force of the spring 52 so that the color measurement instrument 26 lowers onto the foot 56. As the unit 12 lowers, the target arm 54 telescopes into the housing 20 within the tracks 50. As the unit 12 is pushed against the foot 56, a plunger switch 160 is depressed to automatically actuate the color measurement instrument to take a spot reading. When the reading is complete, the manual pressure on the unit 12 is released, whereupon the unit rises because of the spring force of the spring 52 to the position illustrated in FIGS. 2 and 6. The control and color measurement software for spot reading are well known to those skilled in the art.

Figure 14:
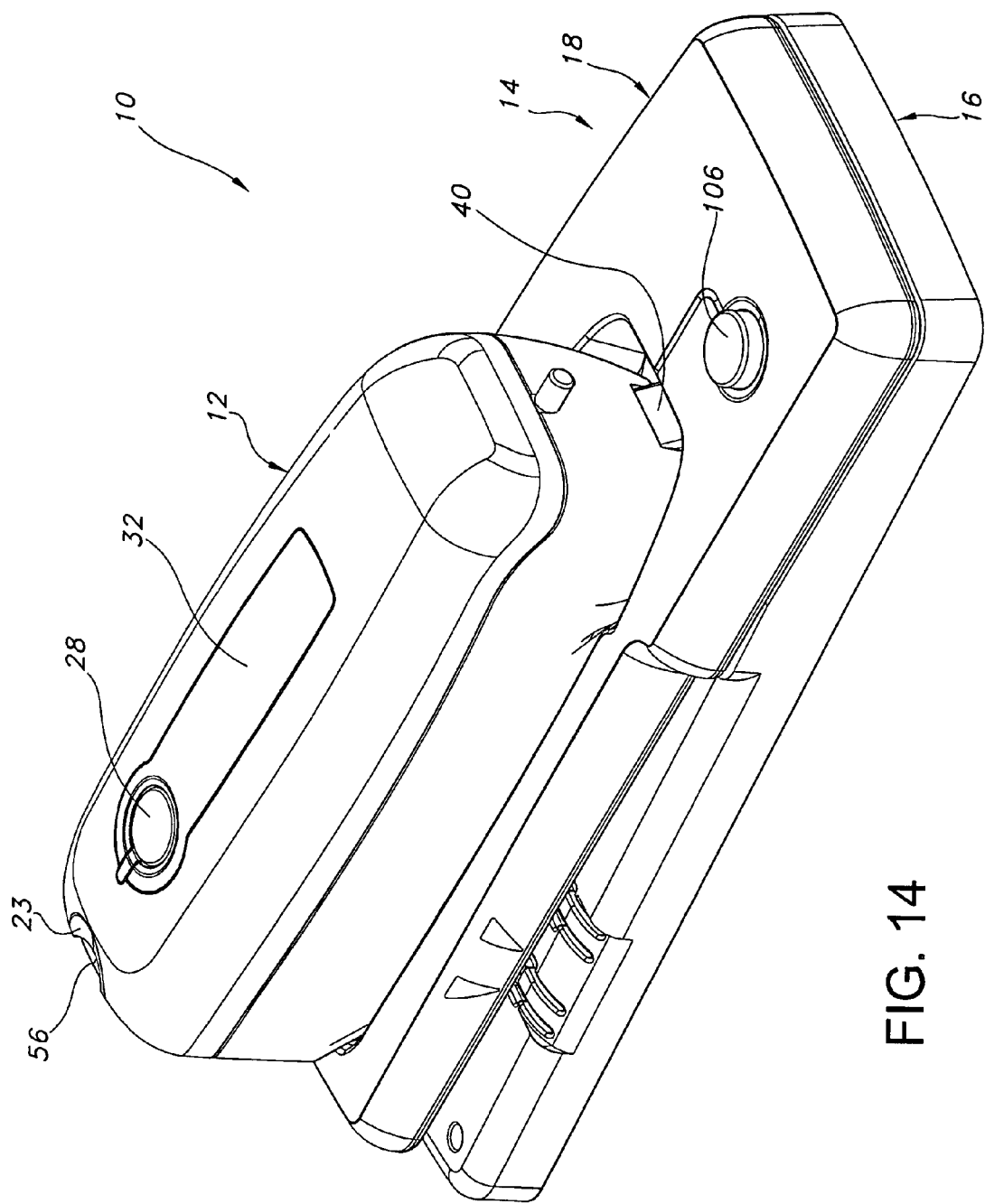
FIG. 14 is a view similar to FIG. 1 but showing the cradle teetered to the open position.
Figure 15:
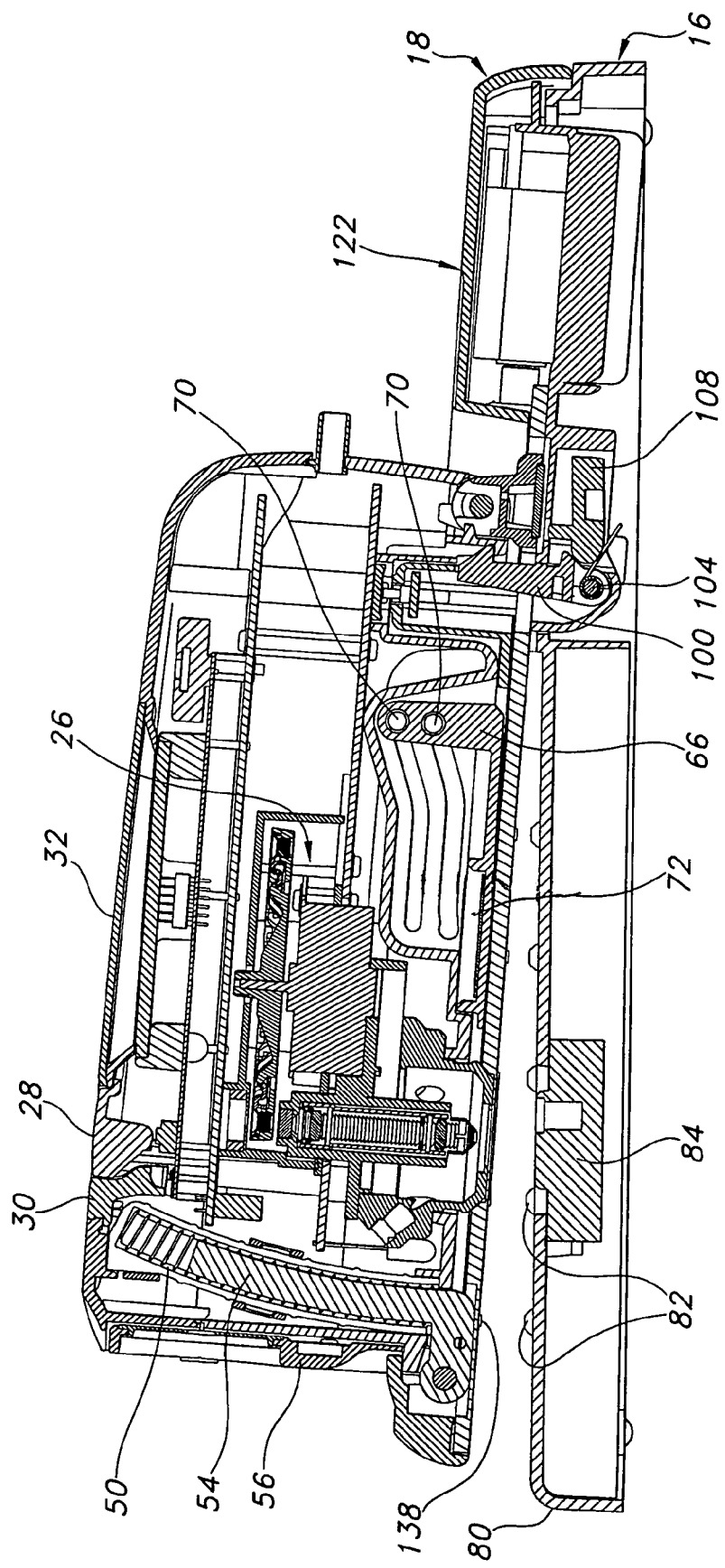
FIG. 15 is a sectional view similar to FIG. 9 but showing the cradle teetered to the open position.

FIGS. 14 and 15 are similar to FIGS. 1 and 9, respectively. However, they show the cradle 18 rocked or teetered to lift the handheld unit 12 from the idler rollers 82 and thereby open the sample strip area. This teetering or lifting is accomplished applying manual downward pressure to the right end or portion of the cradle 18 (when viewed as in FIGS. 14-15). This rocks or teeters the cradle about the fulcrum platform 92 (see FIG. 3) so that the left portion of the cradle 18 rises above the base 16. This motion lifts the handheld unit 12 from the base 16 permitting (a) unusually thick or thin sample media to be loaded, (b) sample jams to be corrected, (c) sample alignment be corrected or adjusted, and (d) the sample transportation area to be visually inspected.

The above description is that of a current embodiment of the invention. Various alterations and changes can be made without departing from the spirit and broader aspects of the invention as defined in the appended claims, which are to be interpreted in accordance with the principles of patent law, including the doctrine of equivalents.

The invention claimed is:

1. A color measurement unit comprising:
   a housing;
   a color measurement engine within said housing;
   a self-storing calibration assembly including a calibration plaque and an arm supporting said calibration plaque on said housing, said self-storing calibration assembly movable between an operative position in which said calibration plaque is aligned with said color measurement engine and a storage position in which said calibration plaque is unaligned with said color measurement engine.

2. A color measurement unit as defined in claim 1 wherein:
   said housing defines a recess; and
   at least a portion of said self-storing calibration assembly is located within said recess when said self-storing calibration assembly is in the storage position.

3. A color measurement unit as defined in claim 1 wherein;
   said arm defines a pocket; and
   said calibration plaque is located within said pocket.

4. A color measurement unit as defined in claim 3 wherein:
   said housing defines a recess; and
   said pocket and said calibration plaque are located within said recess when said self-storing calibration assembly is in the storage position.

5. A color measurement unit as defined in claim 1 further comprising a docking unit, said color measurement unit being selectively docked in said docking unit, said self-storing calibration assembly being configured to move to the operative position when said color measurement unit is undocked, said self-storing calibration assembly being incapable of moving to the operative position when said color measurement unit is docked.

6. A color measurement instrument comprising:
   a color measurement engine; and
   a self-storing calibration assembly including a calibration plaque, said self-storing calibration assembly movable between an active position in which said calibration plaque is aligned with said color measurement engine and a storage position in which said calibration plaque is unaligned with said color measurement engine, said self-storing calibration assembly connected to said color measurement instrument in both positions;
   wherein said self-storing calibration assembly comprises:
   a support arm defining a pocket; and
   a calibration plaque located within said pocket.

* * * * *